(12) United States Patent
Fackler et al.

(10) Patent No.: US 7,519,541 B2
(45) Date of Patent: Apr. 14, 2009

(54) SYSTEM AND METHOD IN A COMPUTER SYSTEM FOR MANAGING A NUMBER OF ATTACHMENTS ASSOCIATED WITH A PATIENT

(75) Inventors: James C. Fackler, Baltimore, MD (US); Deepa Deendar, Shawnee, KS (US); Amy Francois, Lee's Summit, MO (US); Michelle Moseman, Kansas City, MO (US); Stephanie Rogers, Kansas City, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 773 days.

(21) Appl. No.: 10/767,319

(22) Filed: Jan. 29, 2004

(65) Prior Publication Data
US 2005/0027563 A1 Feb. 3, 2005

Related U.S. Application Data

(60) Provisional application No. 60/443,380, filed on Jan. 29, 2003.

(51) Int. Cl.
*G06Q 10/00* (2006.01)
(52) U.S. Cl. ............................................... 705/2; 705/3
(58) Field of Classification Search ..................... 705/2, 705/3
See application file for complete search history.

(56) References Cited

U.S. PATENT DOCUMENTS

| 5,651,775 | A * | 7/1997 | Walker et al. ................ 604/207 |
| 6,527,558 | B1 * | 3/2003 | Eggert et al. ................ 434/262 |
| 6,557,558 | B1 * | 5/2003 | Tajima et al. ................ 128/897 |
| 6,650,930 | B2 * | 11/2003 | Ding .......................... 600/436 |
| 6,844,884 | B2 * | 1/2005 | Balloni et al. ................ 345/629 |
| 2001/0041992 | A1 * | 11/2001 | Lewis et al. ..................... 705/3 |
| 2002/0038392 | A1 * | 3/2002 | De La Huerga ................ 710/8 |
| 2002/0049362 | A1 * | 4/2002 | Ding .............................. 600/1 |
| 2003/0135087 | A1 * | 7/2003 | Hickle et al. ................... 600/26 |
| 2003/0200119 | A1 | 10/2003 | Lewis et al. |
| 2004/0176984 | A1 * | 9/2004 | White et al. .................... 705/2 |

* cited by examiner

*Primary Examiner*—C Luke Gilligan
*Assistant Examiner*—Neal R Sereboff
(74) *Attorney, Agent, or Firm*—Shook, Hardy & Bacon, L.L.P.

(57) ABSTRACT

A method and system suitable for managing a number of attachments is provided. The method includes the steps of displaying attachment details for the plurality of attachments, displaying a representation of at least a portion of a human body; generating a graphical indicia for each attachment and displaying the indicia at the appropriate location on the human representation; upon receipt of input from a user, displaying at least one task associated with at least one attachment; and upon receipt of input from a user, providing a clinical document or image associated with an attachment.

15 Claims, 11 Drawing Sheets

| Type | Location | Date | Order | Order Details |
|---|---|---|---|---|
| Peripheral venous | R Hand | 1/6 | Dextrose 5% + 20 meq KCL | 1000 ml, 100 ml/hr Infuse over 8 hours, IV |
| Peripheral venous hep lock | L Forearm | 1/8 | Ancef | 1 gm, IVPB, q8hrs, 11/26/02 |
| Ductube | | | Jevity | 100ml/hr |
| Central venous - triple lumen | L Subclavian | 1/5 | Triple lumen catheter | |
| Foley Catheter | Urethra | 1/6 | Foley Catheter | to DD |
| Chest Tube | RLL | 1/2 | Chest Tube | -30 mH20 |
| Chest Tube | | | Chest Tube | -30 mH20 |
| Nephrostomy | R | 1/1 | Nephrostomy | to DD |
| Monitoring | | | | |
| Ventilator | Trachea | 1/5 | Ventilator | FIO2 30%, PIP 20, Rate 12 |
| Balloon Pump | L Fem | 1/3 | Balloon Pump | 21 |

Legend:
- Intake
- Output
- Monitoring
- Culture Info
- Notes
- Task

FIG. 3B.

| Type | Location | Date | Order | Order Details |
|---|---|---|---|---|
| Peripheral venous | R Hand | 1/6 | Dextrose 5% + 20 meq KCL | 1000 mL, 100 ml/hr Infuse over 8 hours, IV |
| Peripheral venous hep lock | L Forearm | 1/8 | Ancef | 1 gm, IVPB, q8hrs, 11/26/02 |
| Ductube | | | Jevity | 100ml/hr |
| Central venous - triple lumen | L. Subclavian | 1/5 | Triple lumen catheter | |
| Foley Catheter | Urethra | 1/6 | Foley Catheter | to DD |
| Chest Tube | RLL | 1/2 | Chest Tube | -30 mH2O |
| Chest Tube | | | Chest Tube | -30 mH2O |
| Nephrostomy | R | 1/1 | Nephrostomy | to DD |
| Ventilator | Trachea | 1/5 | Ventilator | FIO2-30%, FiP-20, Rate 12 |
| Balloon Pump | L Fem | 1/3 | Balloon Pump | 2:1 |

Microbiology Result Details - Micro, Noah C. - MRN000-002-74

Amended Final Report - Friday, December 28, 2001
11:17 AM -
>100,000 cfu/ml Staphylococcus species[1] Gram
Positive Cocci (1) Staphylococcus species was previously reported
incorrectly as Gram Negative Rod. Change to correct
organism name was made in Preliminary Report issued
on 27/12/01.
Incorrect reporting due to: biochemical mislabeling.

Amended Final Report - Friday, December 28, 2001
11:16 AM -
>100,000 cfu/ml Staphylococcus species[1]

(1) Staphylococcus species was previously reported
incorrectly as Gram Negative Rod. Change to correct
organism name was made in Preliminary Report issued

Naso-Orogastric Tube Care - Harper, Lennard L.
*Performed on: 1/11/2003    1013    By: Douglas, Peggy*

Nasogastric/Orogastric Tube Care

Tube Activity
- ○ Discontinue
- ○ Insert
- ○ Irrigated with other
- ○ Irrigated with water
- ○ Repositioned
- ○ Sample
- ○ Secure
- ○ Other:

Tube Location
- ○ Nostril, Left
- ○ Nostril, Right
- ○ Oral

Tube Size
- ○ 5 French
- ○ 6 French
- ○ 8 French
- ○ 10 French
- ○ 12 French
- ○ 14 French
- ○ 16 French
- ○ 18 French
- ○ Other:

Tube Type
- ○ Nasoduodenal
- ○ Nasogastric tube
- ○ Orogastric
- ○ Other:

Drainage Method
- ○ Clamped
- ○ Continuous suction
- ○ Gravity
- ○ Low intermittent suction
- ○ Other:

Drainage Description
- ☐ Bile
- ☐ Blood-tinged
- ☐ Bloody
- ☐ Clear
- ☐ Coffee ground
- ☐ Fecal odor
- ☐ Mucous
- ☐ Pink
- ☐ Red
- ☐ Undigested food
- ☐ Watery
- ☐ Other:

Initial Gastric Tube Output
_____ mL

Gastric Occult Blood
- ○ Negative
- ○ Positive

Placement Confirmed By
- ☐ Aspiration
- ☐ Auscultation
- ☐ pH testing
- ☐ X-ray
- ☐ Other:

Amount of Irrigant

Procedure Tolerance
- ○ Good
- ○ Fair
- ○ Poor

Unexpected Response

Naso/Orogastric

FIG. 10.

SYSTEM AND METHOD IN A COMPUTER SYSTEM FOR MANAGING A NUMBER OF ATTACHMENTS ASSOCIATED WITH A PATIENT

CROSS-REFERENCE TO RELATED APPLICATIONS

This application claims the benefit of priority of U.S. Provisional Application No. 60/443,380 filed on Jan. 29, 2003.

STATEMENT REGARDING FEDERALLY SPONSORED RESEARCH OR DEVELOPMENT

Not applicable.

TECHNICAL FIELD

The present invention relates to a system and method in a computer system for managing a number of attachments associated with a patient.

BACKGROUND OF THE INVENTION

A number of attachments are associated with a patient in the provision of modern healthcare, particularly in a critical care or intensive care setting. As the number of attachments and functions provided by these attachments increases, the potential for adverse and other atypical events increases. As such, a need exists for a system and method for managing a number of attachments associated with a patient.

BRIEF SUMMARY OF THE INVENTION

In accordance with the invention, a system and method in a computer system are provided for managing a number of attachments associated with a patient. The method includes the steps of displaying attachment details for the plurality of attachments, displaying a representation of at least a portion of a human body; generating a graphical indicia for each attachment and displaying the indicia at the appropriate location on the human representation; upon receipt of input from a user, displaying at least one task associated with at least one attachment; and upon receipt of input from a user, providing a clinical document or image associated with an attachment.

Additional advantages and novel features of the invention will be set forth in part in a description which follows, and in part will become apparent to those skilled in the art upon examination of the following, or may be learned by practice of the invention.

BRIEF DESCRIPTION OF THE DRAWINGS

The present invention is described in detail below with reference to the attached drawing figures, wherein.

DETAILED DESCRIPTION OF THE INVENTION

Figure 1:
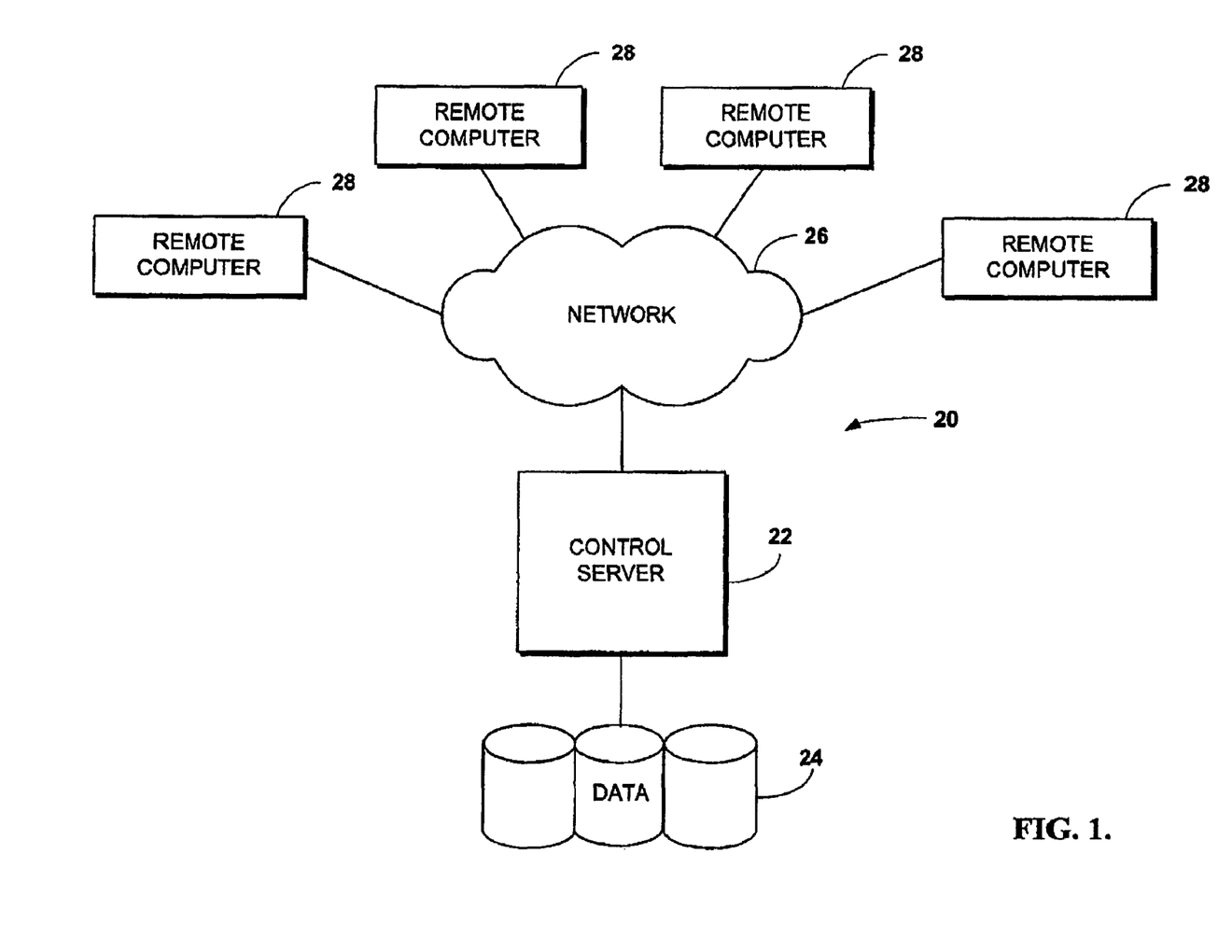
FIG. 1 is a schematic diagram of a suitable computing system environment for use in implementing the present invention.

The present invention provides a method and system for managing a number of attachments associated with a patient. FIG. 1 illustrates an example of a suitable medical information computing system environment 20 on which the invention may be implemented. The medical information computing system environment 20 is only one example of a suitable computing environment and is not intended to suggest any limitation as to the scope of use or functionality of the invention. Neither should the computing environment 20 be interpreted as having any dependency or requirement relating to any one or combination of components illustrated in the exemplary environment 20.

The invention is operational with numerous other general purpose or special purpose computing system environments or configurations. Examples of well-known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The invention may be described in the general context of computer-executable instructions, such as program modules, being executed by a computer. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media, including memory storage devices.

With reference to FIG. 1, an exemplary medical information system for implementing the invention includes a general purpose computing device in the form of server 22. Components of server 22 may include, but are not limited to, a processing unit, internal system memory, and a suitable system bus for coupling various system components, including database cluster 24 to the control server 22. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Server 22 typically includes therein or has access to a variety of computer readable media, for instance, database cluster 24. Computer readable media can be any available media that can be accessed by server 22, and includes both volatile and nonvolatile media, removable and nonremovable media. By way of example, and not limitation, computer readable media may comprise computer storage media and communication media. Computer storage media includes both volatile and nonvolatile, removable and nonremovable media implemented in any method or technology for storage of information, such as computer readable instructions, data structures, program modules or other data. Computer storage media includes, but is not limited to, RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by server 22. Communication media typically embodies computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media such as acoustic, RF, infrared and other wireless media. Combinations of any of the above should also be included within the scope of computer readable media.

The computer storage media, including database cluster 24, discussed above and illustrated in FIG. 1, provides a storage of computer readable instructions, data structures, program modules, and other data for server 22.

Server 22 may operate in a computer network 26 using logical connections to one or more remote computers 28. Remote computers 28 can be located at a variety of locations in a medical environment, for example, but not limited to, hospitals, other inpatient settings, pharmacies, a clinician's office, ambulatory settings, testing labs, medical billing and financial offices, hospital administration, and a patient's home environment. Clinicians include, but are not limited to, the treating physician, specialists such as surgeons, radiologists and cardiologists, emergency medical technicians, physician's assistants, nurse practitioners, nurses, nurse's aides, pharmacists, dieticians, microbiologists, and the like. The remote computers may also be physically located in non-traditional medical care environments so that the entire health care community is capable of integration on the network. Remote computers 28 may be a personal computer, server, router, a network PC, a peer device or other common network node, and may include some or all of the elements described above relative to server 22. Computer network 26 may be a local area network (LAN) and/or a wide area network (WAN), but may also include other networks. Such networking environments are commonplace in offices, enterprise-wide computer networks, intranets and the Internet. When utilized in a WAN networking environment, server 22 may include a modem or other means for establishing communications over the WAN, such as the Internet. In a networked environment, program modules or portions thereof may be stored in server 22, or database cluster 24, or on any of the remote computers 28. For example, and not limitation, various application programs may reside on the memory associated with any one or all of remote computers 28. It will be appreciated that the network connections shown are exemplary and other means of establishing a communications link among the computers may be used.

A user may enter commands and information into server 22 or convey the commands and information to the server 22 via remote computers 28 through input devices, such as keyboards, pointing devices, commonly referred to as a mouse, trackball, or touch pad. Other input devices may include a microphone, satellite dish, scanner, or the like. Server 22 and/or remote computers 28 may have any sort of display device, for instance, a monitor. In addition to a monitor, server 22 and/or computers 28 may also include other peripheral output devices, such as speakers and printers.

Although many other internal components of server 22 and computers 28 are not shown, those of ordinary skill in the art will appreciate that such components and their interconnection are well known. Accordingly, additional details concerning the internal construction of server 22 and computer 28 need not be disclosed in connection with the present invention.

The method and system of the present invention manages a number of invasive attachments associated with a patient. Although the method and system are described as being implemented in a WINDOWS operating system operating in conjunction with a comprehensive healthcare network, one skilled in the art would recognize that the method and system can be implemented in any system supporting the receipt and processing of clinical information.

Figure 2:
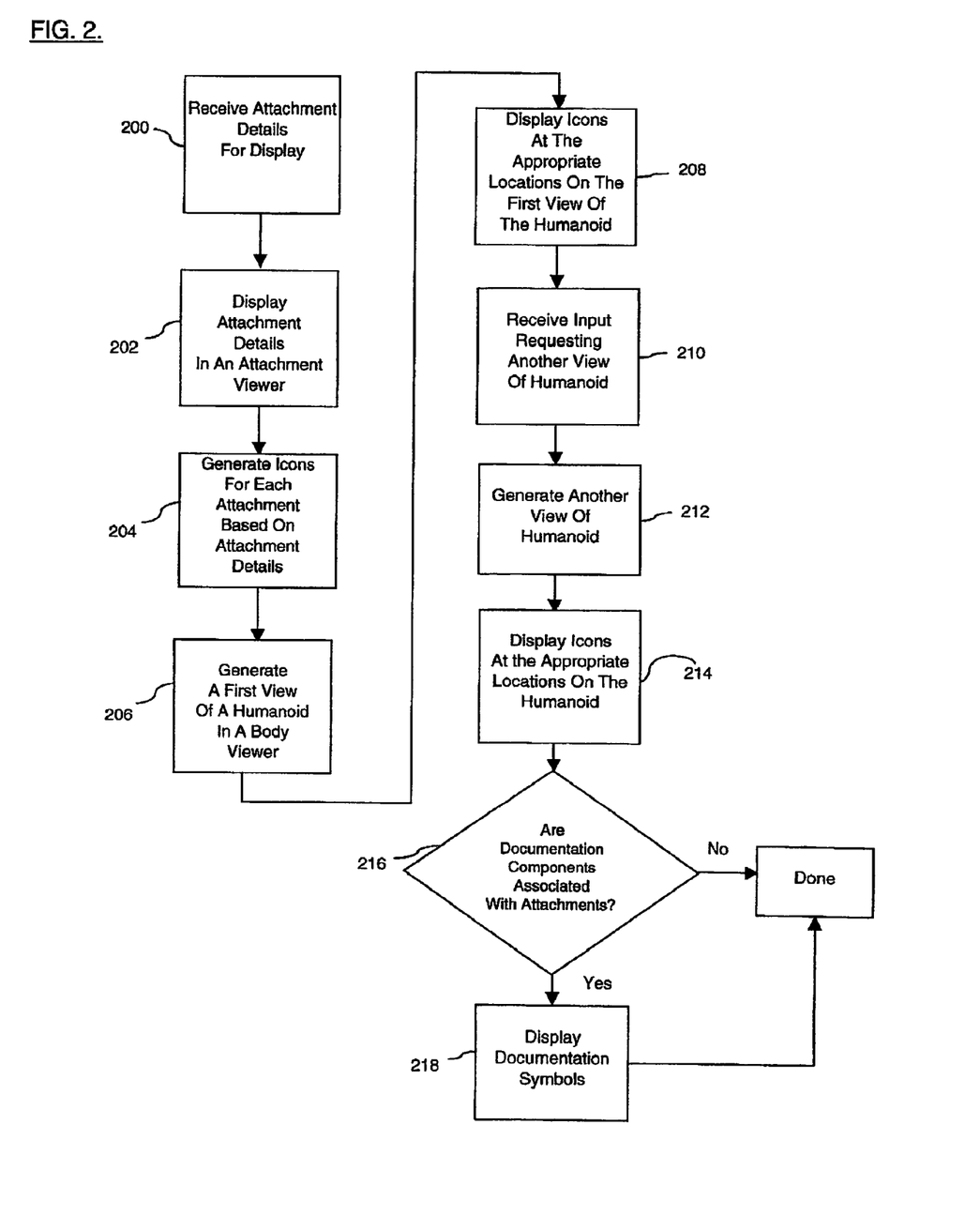
FIG. 2 is a flow diagram illustrating a preferred method for managing a number of attachments associated with a patient.

With reference to FIG. 2, in the first embodiment of the present invention, a system and method for managing a number of attachments associated with a patient is shown. For purposes of the present invention, an "attachment" or "line" is a connection from any medical device that is attached, inserted, laid upon or otherwise physically associated with a patient. Further, for purposes of this invention, an attachment includes but is not limited to a temporary device such as a peripheral IV, a central line, a PA catheter, an arterial line, temporary pacemaker wires, epidural catheters, subdural catheters, endotracheal tubes, chest tubes, surgical drains and urinary catheters and implantable devices such as VP shunts, tracheostomies, cardiac pacemakers, medication pumps, implanted central lines, dialysis shunts and vascular filters. Thus, the attachment type may be identified by the physical connection or the medical device associated with connection.

In an initial step 200, the system of the present invention receives details regarding the attachments associated with the patient. The attachment details may include a number of elements of information relevant to the attachment. For example, the attachment details include without limitation insertion data, use history, microbiological data and device-specific data, and details about the clinician or staff responsible for the attachment. "Insertion data" includes information about the type of medical device associated with the patient, the location of the device relative to the patient, the date and time the attachment was associated with the patient, the identification of the care provider who associated the attachment with the patient and/or the responsible clinician for the attachment, the conditions in which the physical attachment was made (i.e. sterile or emergency), and operative information associated with the attachment. Also, insertion data may include the use history of attachment including order identification, order details and the historic setting of a physical device. An order is a request for one or more procedures to be performed. For instance, an order may specify a particular medication, and the dosage, form, route and frequency of the medication. "Microbiological data" includes the results of a culture performed at the site associated with the attachment. "Device-specific data" includes information related to the device associated with the attachment. By means of example and not limitation, if the attachment type is a central line, the device specific data may included data about the location of the tip of the line, the method used to secure the line, the wave form, the identification of the monitoring lumen of the line and a chest x-ray. In another example, if the device is a PA catheter, data about the tip location, wave form snippets from insertion, wedges or chest x-ray may be relevant device-specific data. In another example, if the device is a endotracheal tube, the device-specific data may include the size of the tube, cuff pressure, depth and tube leak.

As described further below, the attachment details may be received in a number of ways. For example, the attachment details may be input directly into the fields of the present system as described below and stored in the storage components of the operating environment. Alternatively, if an active clinical order is associated with an attachment, the order may be associated with one of the attachments and populated in the system of the present invention. For example, as known in the order, an order may be received by means of a computerized physician order entry (CPOE) system and populated into the system of the present invention. The order information is preferably stored as part of an electronic medical record (EMR) with the database (database cluster 24 in FIG. 1). Commonly, when an order is populated in the system of the present invention, the user will be prompted to associate the order with an attachment represented by the system (or create a new attachment to which the order may be associated as described below).

Figure 3A:
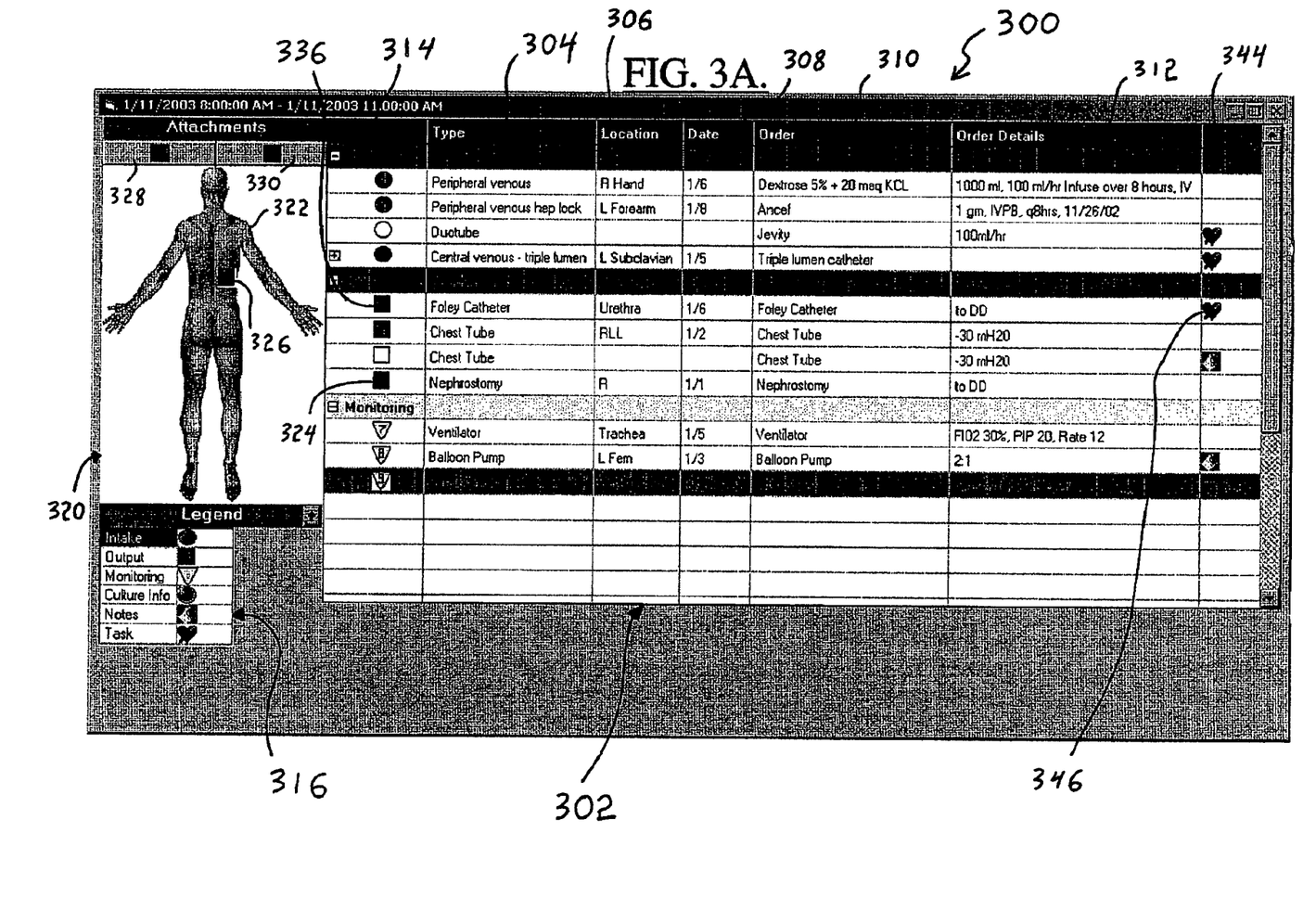
FIG. 3A is a first exemplary screen shot of an attachment management view illustrating a patient having multiple attachments in accordance with the system and method of the present invention.

At step 202, the attachment details are displayed. With reference to FIG. 3A, an attachment management view 300 displays the attachment details textually in an attachment viewer 302. Preferably, the attachment details are stored in a tabular form. Each attachment is represented by a row in the table. In some cases, multiple orders are associated with a single attachment and multiple rows may be populated for the attachment. Unattached lines (such as the arterial line represented in FIG. 3A) have a gray background to provide a visual indication that the line is unattached. In a preferred embodiment, the type of attachment is displayed in a first column 304, the location of the attachment is displayed in a second column 306, a date associated with the attachment is displayed in a third column 308, the type of order is displayed in a fourth column 310 and associated order details are displayed in a fifth column 312. Additional attachment details are contemplated by this invention including free text entries.

With reference to FIG. 2, at step 204, an icon is generated for each attachment based on the attachment details. For purposes of the present invention, the icon may be a symbol, design or other visual indicia. With reference to FIG. 3A, in a preferred embodiment, the icons generated for each attachment are displayed in a column 314 and are shaped according to the function of the attachment. Specifically, as graphically depicted in an optional legend portion 316, attachments for intake into the patient are represented by a circular icon, attachments for output from the patient are represented by a square-shaped icon and attachments for monitoring the patient are represented by a triangular icon. As shown in FIG. 3A, the attachments are preferably organized within the tabular attachment viewer in accordance with the functions (intake, output or monitoring) represented by the icons. In a preferred embodiment, a number (or other unique identifier) is applied to each icon. Also, for each attachment that is currently attached, the icon is shaded or otherwise distinguished from inactive attachments which are not shaded.

The system determines the appropriate icon either based on information in the system or by manual input of a user. For instance, some attachments may always be used for monitoring the patient, and the icon associated with monitoring always used for the attachment type. In other cases, the attachment details may not indicate which icon should be displayed for the particular attachment. For example, an NG tube attachment may be used for feeding and require the icon associated with input, or may be used for suctioning and require the icon for output. In those cases, a user may select a particular attachment and identify the appropriate icon based on the function of the attachment by right-clicking on the line or any of a number of other known input means. The number assigned to the icon representing each attachment may also be established by the system or through manual input of the user.

With reference to FIG. 2, at step 206, the system displays a first view of a humanoid in a body viewer. As best illustrated in FIG. 3A, the attachment management view includes a body viewer 320 that is displayed proximate attachment viewer 302. In FIG. 3A, a rear view of the humanoid is generated. Preferably, when the system of the present invention is used, a default view of the humanoid is displayed. In this case, the body viewer 320 includes a first rear view of a humanoid 322. Other graphical representations of all or part of the human body are contemplated by this invention.

Next, with reference back to FIG. 2, the system displays a number of icons (matching the aforementioned icons) at the appropriate location on the first view of the humanoid. As best illustrated in FIG. 3A, each icon associated with a location on the patient's body that is viewable on the humanoid is displayed. On the rear view of the humanoid, the physical location of only one of attachments is viewable. Specifically, in the attachment viewer, an icon 324 that is associated with a nephrostomy attachment located on the right rear of the patient is viewable. As such, an icon 326 identical to the icon 324 is displayed on the lower right back of the humanoid represented in the body viewer 320. The number '6' located on the icons 324 and 326 associates the icon in the body viewer with the attachment details in the attachment viewer. Since the nephrostomy (or attachment "6") is the only currently attached and viewable entry in the user interface of FIG. 3A, the row for is displayed in a darker type to distinguish the attachment from the others. Alternatively, the attachments that are viewable in the current view of the humanoid may be highlighted to distinguish the attachment from the other attachments on the attachment viewer.

With reference to FIG. 2, the system receives input requesting another view of the humanoid. Specifically, as shown in FIG. 3A, a first control 328 and a second control 330 in the body viewer are capable of receiving user input requesting another view of humanoid. Preferably, several views of the humanoid are available to demonstrate the location of the attachments associated with the patient. In the preferred example, when a user selects one of the controls 328 or 330, the humanoid is rotated. Zooming and other typical visual controls are also contemplated by this invention to obtain additional views.

Figure 3B:
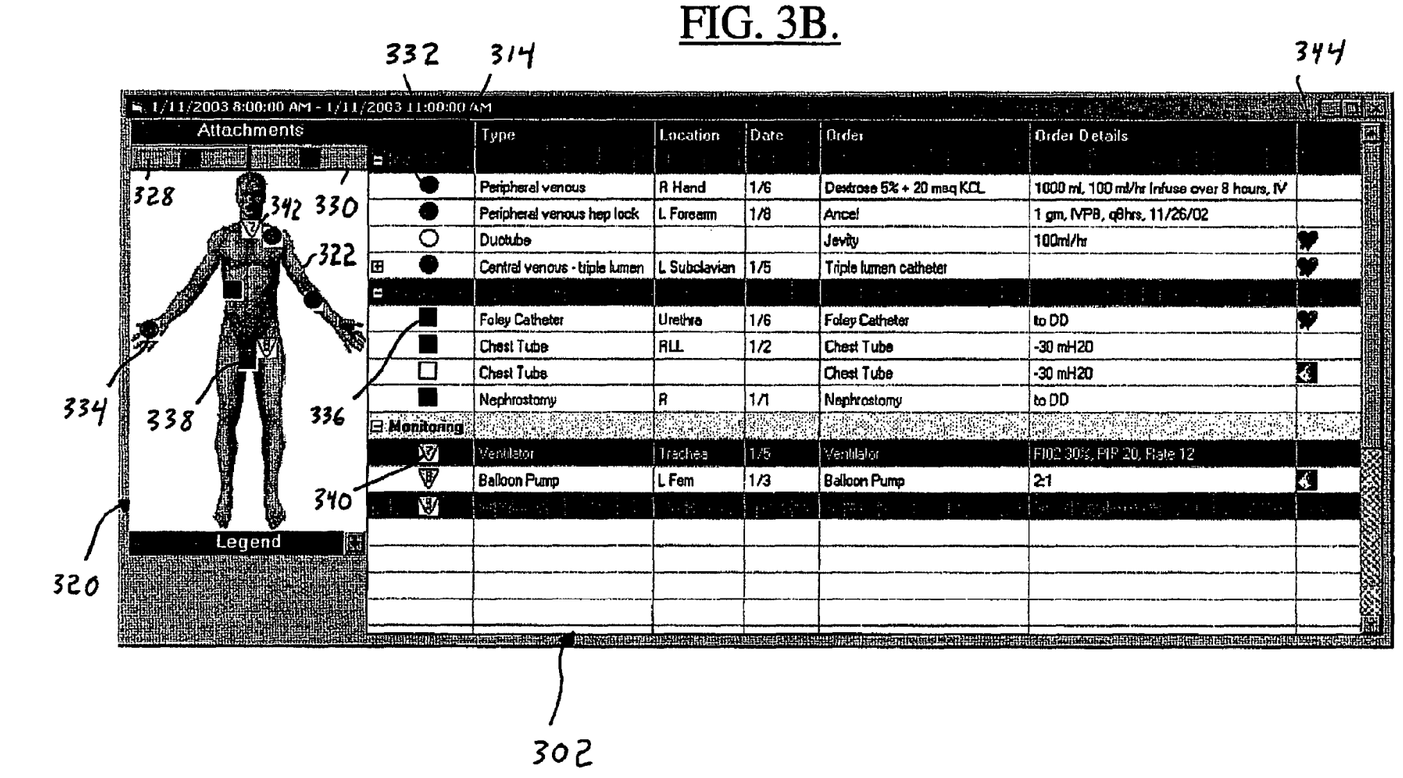
FIG. 3B is a second exemplary screen shot of an attachment management view for the patient of FIG. 3A.

With brief reference to FIG. 2, after input requesting another view of the humanoid is received at step 210, the system generates another view of the humanoid at step 212 and displays icons at the appropriate locations on the humanoid at step 214. With reference to FIG. 3B, another view of the humanoid 322 is displayed in body viewer 320. The attachment details stored in the database cluster (or other part of the operating environment) are queried to determine the location of each attachment, and icons corresponding the icons in column 314 of attachment viewer 302 are located on the humanoid. By way of example, an icon 332 represents a peripheral venous attachment located in the right hand of the patient for an order of "dextrose 5%+20 KCL" with order details specifying that 1000 ml are to be delivered at a rate of 100 ml per hour over eight hours intravenously. In a preferred embodiment, the icon 332 is circular since the attachment is for intake, and is given the number "1" for purposes of identification. An identical icon 334 is located in the body viewer 320 at the right hand of the humanoid. In another example, an icon 336 in the attachment viewer represents a Foley catheter located in the urethra. The attachment was made on January 6th based on an order for the Foley catheter containing an order detail specifying that the catheter go to a drain. The icon 336 is square-shaped since the attachment is for output and includes the numeral "4" for purposes of identification. A similar icon 338 associated with the icon 336 is located at the outlet for the urethra on the humanoid 322 in body viewer 320. In another example, an icon 340 in the attachment viewer represents a ventilator located in the trachea on January 5th. The ventilator is placed on the patient in response to an order for the ventilator with the order details of "FIO2 30%, PIP 20, Rate 12." The icon 340 is triangular since it represents monitoring and includes the numeral "7" for purposes of identification. A similar icon 342 is located on humanoid 322 at the trachea. Preferably, each of these icons 334, 338 and 342 are located on the humanoid by querying the location field of the database and displaying the icons on the appropriate location on the humanoid based upon this information.

With reference back to FIG. 2, at step 216, the system determines if any documentation components are associated with the attachments. In the preferred embodiment, the documentation components may include a note, a task or a summary of culture information associated with an attachment represented in the attachment management view. If documentation components are associated with the attachments, one or more documentation symbols are generated and included in the attachment view. With reference to FIG. 3A, legend portion 316 includes icons for each type of documentation of the preferred embodiment: a notepad symbol for notes, a heart-shaped symbol for tasks and a symbol indicative of microbiological organisms for culture information. The relevant documentation segments are displayed at a column 344 within the attachment viewer 302. By way of example, based on the clinical information stored in the database cluster, tasks are associated with the Foley Catheter—the attachment associated with icon 336. As such, in column 344 of the attachment viewer, a symbol 346 indicative of the existence task-related documentation is generated by the system and displayed. Each of these documentation components are explained in greater detail with respect to the drill-down flow of FIG. 4 and the screen shots of FIGS. 5-9.

If there are no documentation components associated with an attachment, the method is complete. However, the system continues to poll the data structure for attachment information generated through an order entry system, through user interface into the fields of the system of the present invention by conventional input means or through other systems as known in the art.

Figure 4:
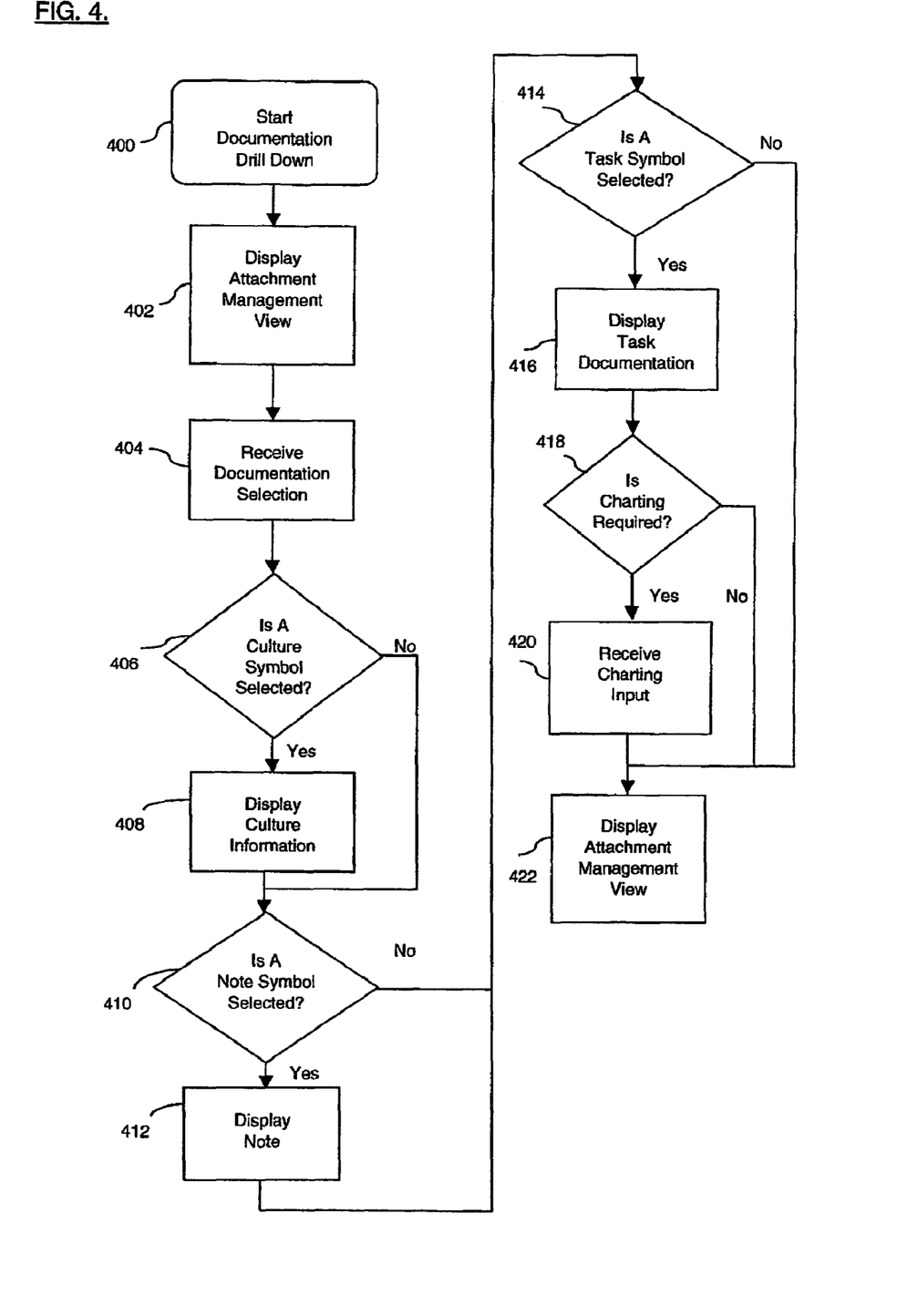
FIG. 4 is a flow diagram illustrating a preferred method for providing documentation, tasks and culture information associated with the attachments of the attachment management view.
Figure 5:
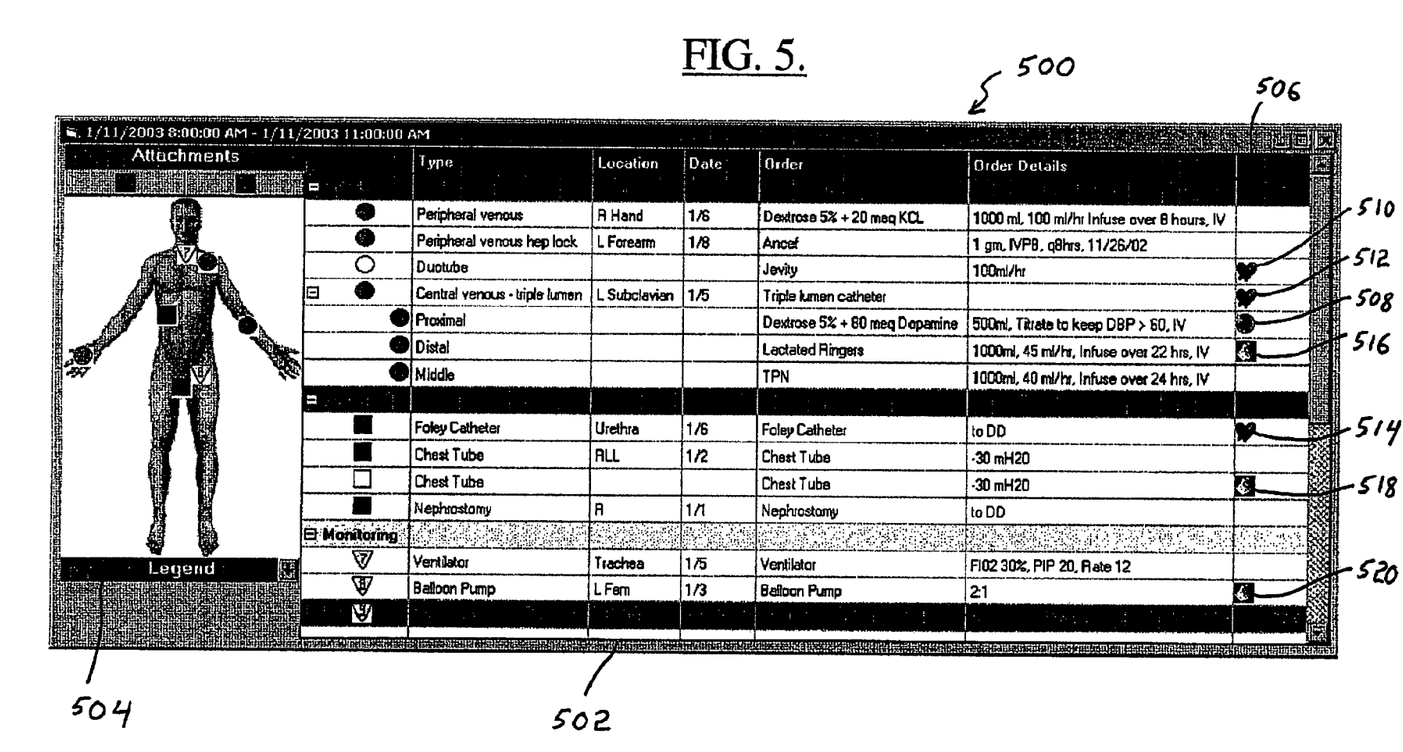
FIG. 5 is a third exemplary screen shot of an attachment management view illustrating the various documentation symbols of the present invention.

With reference to FIG. 4, a subroutine for accessing and entering documentation from the attachment management view is shown. First, at step 400, the documentation drill down routine is initiated. Next, the attachment management view is displayed at step 402 in accordance with the system and method described above. For purposes of this aspect of the present invention, reference is made to an attachment management view 500 of FIG. 5. As shown in an attachment viewer 502, nine attachments are currently attached to the patient: a peripheral venous, a peripheral venous hep lock, a central venous triple lumen, a Foley catheter, a chest tube, a nephrostomy, a ventilator, a balloon pump and an arterial line. (Also, in FIG. 5, the viewable attachments are also displayed on a body viewer 504 of the attachment management view.) With specific reference to the rows in the tabular attachment viewer 502 for the central venous attachment, three orders are associated with the attachment, one for each lumen. To generate these rows completely and accurately, the system queries information from the storage components of the system (FIG. 1) to identify the appropriate lumen to which the order is associated, or receives user input associating an order with a specific lumen.

In another method of receiving the attachment details, the user may import individual orders from another application and associate the order with an attachment in the system of the present invention. For instance, if the user of the system of the present invention accesses a set of orders from a CPOE or similar system, the user could "drag-and-drop" or otherwise associate each order with a lumen of the central venous attachment. As described further below, the ability to store and structure the data relative to all of the attachments provides a number of efficiencies and patient safety benefits in addition to the real-time views provided by the system and method of the present invention.

Figure 6:
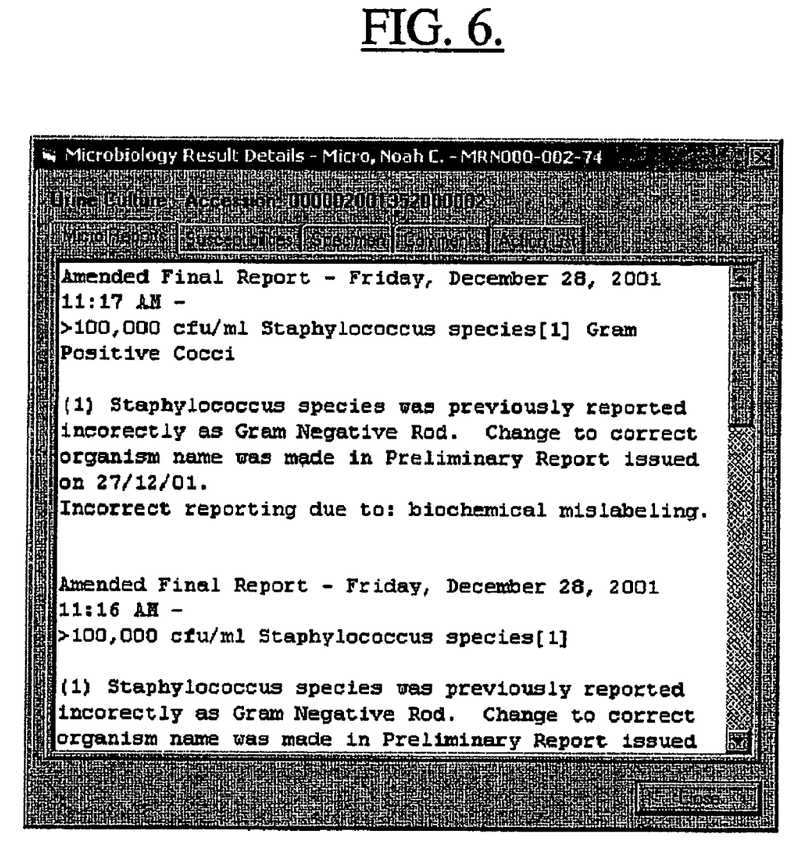
FIG. 6 is an exemplary screen shot displaying microbiology results accessed from the attachment management view.

With reference back to FIG. 4, at step 404, the system receives a document selection. Preferably, with reference to FIG. 5, the attachment viewer includes a column 506 in which the symbols are located. Column 506 includes a culture information symbol 508, three task symbols 510, 512 and 514, and three note symbols 516, 518 and 520. Turning back to FIG. 4, if a culture symbol is selected at step 406, then the system displays culture information at step 408. With reference to FIG. 6, in a preferred embodiment, the culture information displayed includes the microbiology report for the culture taken at the site of the relevant attachment. In addition to reports, various tabs may be selected to display susceptibilities, specimen information, comments and an action list of outstanding tasks. The system of the present invention further contemplates displaying information indicating that the results of the microbiology tests are pending. Thus, in the preferred embodiment of the attachment management view, if a culture information icon is not present, the user of the system can easily ascertain that a culture has not been taken. If the icon is present, the user may select the icon and learn the status, results and tasks associated with the culture.

Figure 7:
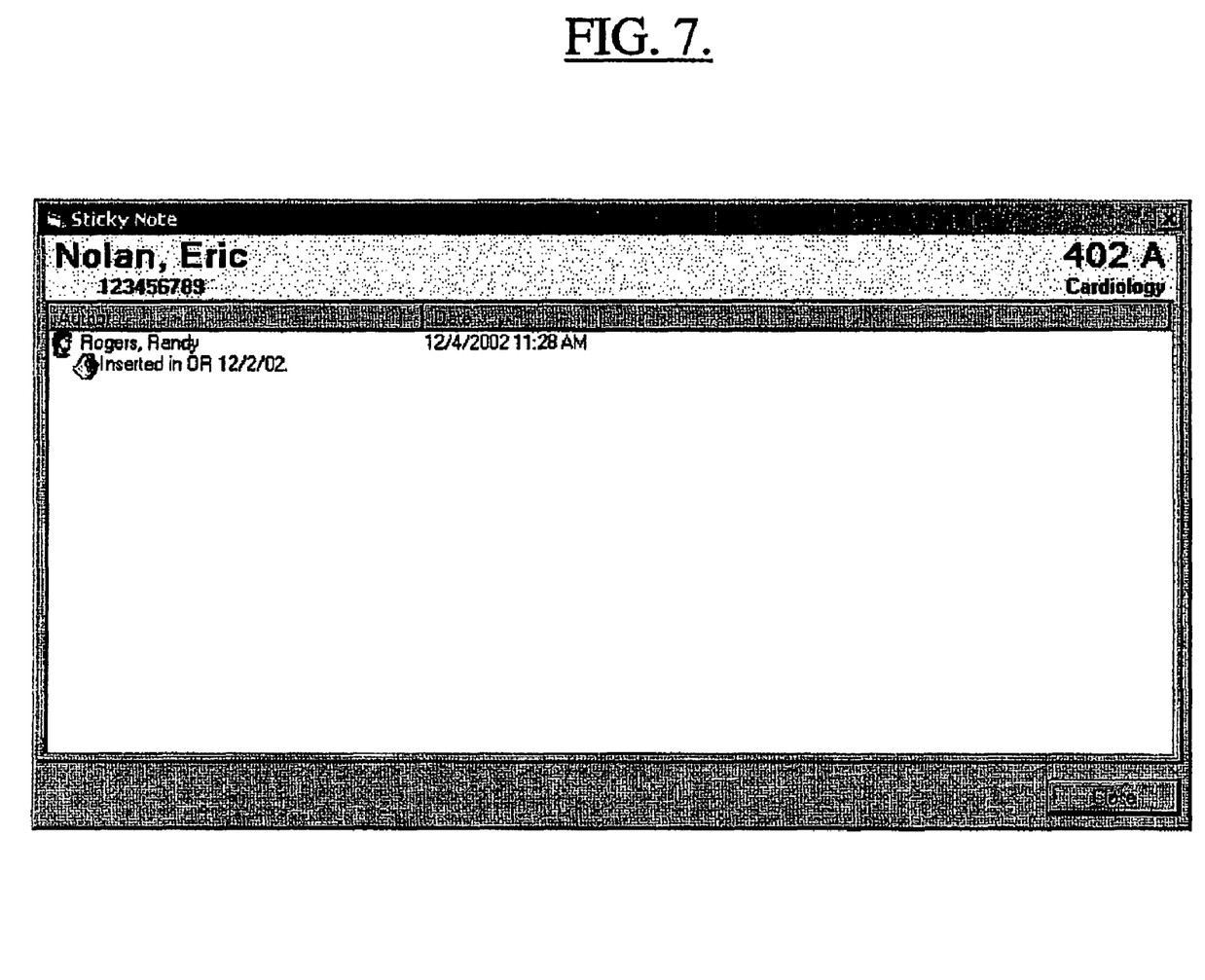
FIG. 7 is an exemplary screen shot displaying a link to a clinical document accessible from the attachment management view.

Returning to FIG. 4, the system determines if a note symbol has been selected at step 410. If a note symbol has been selected, then a note or link to a note is displayed at step 412. Preferably, the selection is made by selecting one of the note symbols in the attachment management view. As shown in FIG. 7, by way of example, a link to a related clinical documents and images may be provided. In this example, a link to a relevant operation report made on Dec. 2, 2002 is provided. The drill-down method related to the note symbols allows the attachment management system to be fully integrated with the other healthcare information technology solutions. In an integrated system, the system and method of the present invention will provide the treating clinicians with all of the necessary information for safely and effectively treating the patient—including documentation and images.

Figure 8:
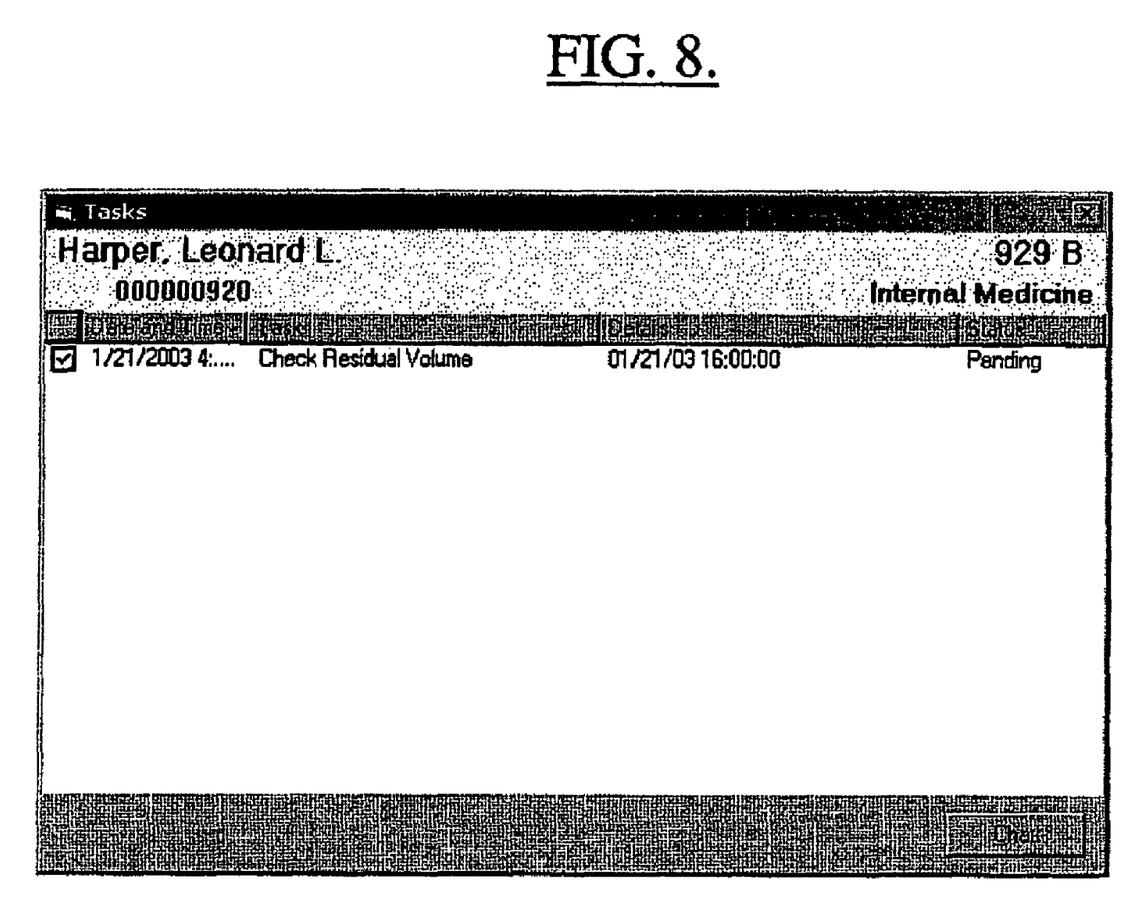
FIG. 8 is an exemplary screen shot displaying a task list accessible from the attachment management view.
Figure 9:
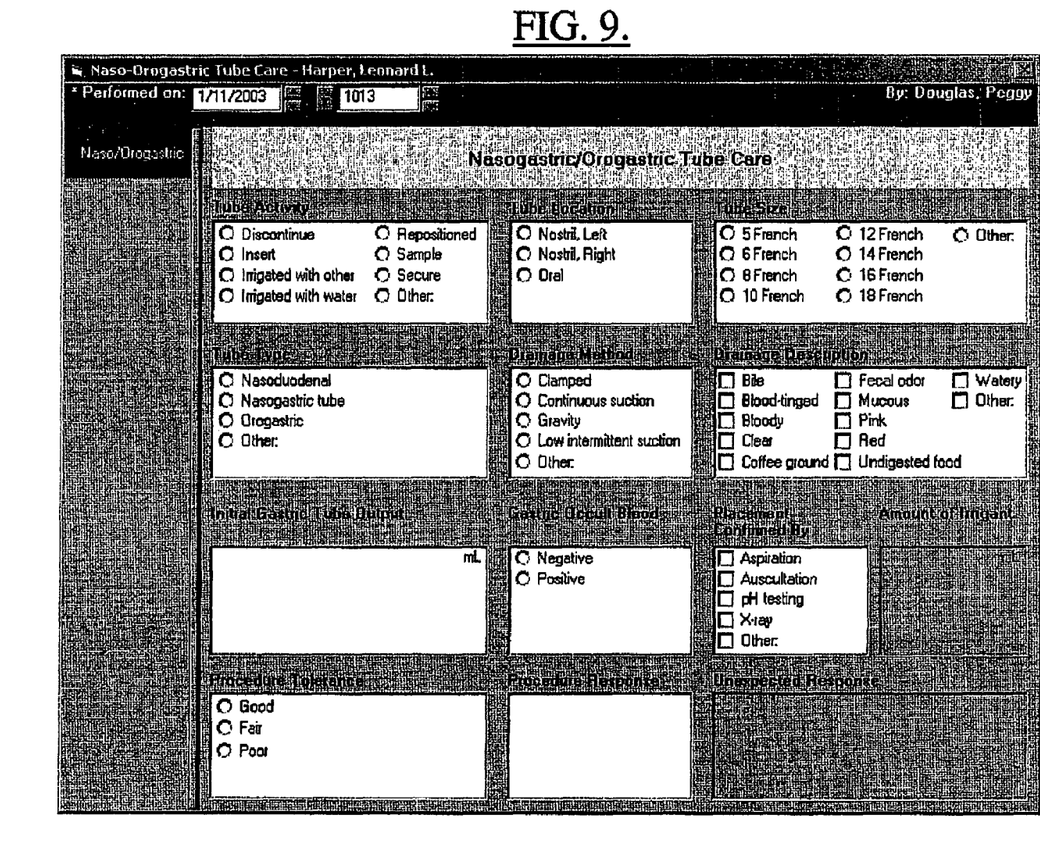
FIG. 9 is an exemplary screen shot of a documentation form to chart relevant details accessible from the task list such as the task list of FIG. 8.

Returning to FIG. 4, the system determines if a task symbol is selected at step 414. If a task symbol has been selected, then task documentation is displayed at step 416. With reference to FIG. 8, a list of tasks associated with the attachment is displayed. In this case, the task of checking residual volume of the attachment is listed along with details associated with the task, the date and time for the task and the status of the task. The integration of the task documentation with the attachment management view allows the user of the system to manage and document tasks for the patient. Also, it is contemplated by the system and method of the present invention to provide alerts to the user of overdue tasks. For instance, the task icon may flash or otherwise display in a different format on the line management view if outstanding tasks are required to be performed. These tasks are critical to maintaining the attachments safely.

Oftentimes, charting is required in addition to displaying the tasks associated with the attachment. With reference to FIG. 4, the system determines if charting is required at step 418. Typically, as shown in FIG. 8, the system may base this determination on user input selecting the charting button on the task display. With reference back to FIG. 4, if charting is required, the system receives charting input at step 420. Preferably, the charting is performed by providing input into a documentation form such as the form illustrated in FIG. 9. Charting through the use of documentation forms is performed in accordance with the methods known to those of ordinary skill in the art. The integration of the charting function with the attachment management view provides an advantageously efficient and safe workflow for the people treating the patient. Finally, with reference to FIG. 4, the attachment management view is displayed at step 422 until additional input is received.

The aspects of the system and method described to this point provide a number of advantages. For example, the combined body viewer and attachment viewer will provide the caregivers with a real-time and a historic view of the treatment of the patient. From a doctor's perspective, this will greatly increase the understanding of the patient's treatment and lead to better care planning and outcomes. From a practical perspective, it will reduce the likelihood of actions and omissions based on confusion among multiple attachments. Similarly, the correlation of the body view with the attachment view will help caregivers to document the appropriate information in the appropriate place. Further, through the symbols and related documentation integrated into the attachment management view, the caregivers can manage tasks, view documents and charts and manage cultures associated with the attachments. Also, the attachment management view may be used to document information directly as described herein.

Additionally, the initiation of new attachments in the line management view is contemplated. For instance, as would be known to those of skill in the art, addition attachments may be added to the attachment view to initiate monitoring, maintenance and documenting the details associated with an attachment. Alternatively, a portion of the humanoid may be selected to initiate a new attachment. In this method, a line would be added to the attachment viewer with the location information populated into the attachment viewer. Also, a list of relevant attachments for that portion of the body provided to assist in completing the information needed to document the attachment.

The system of the present invention is also useful when discharging a patient. The system may be used to insure that all attachments have been removed. More likely, the system may ensure that all of the tasks associated with the safe removal of the attachments have been taken.

Figure 10:
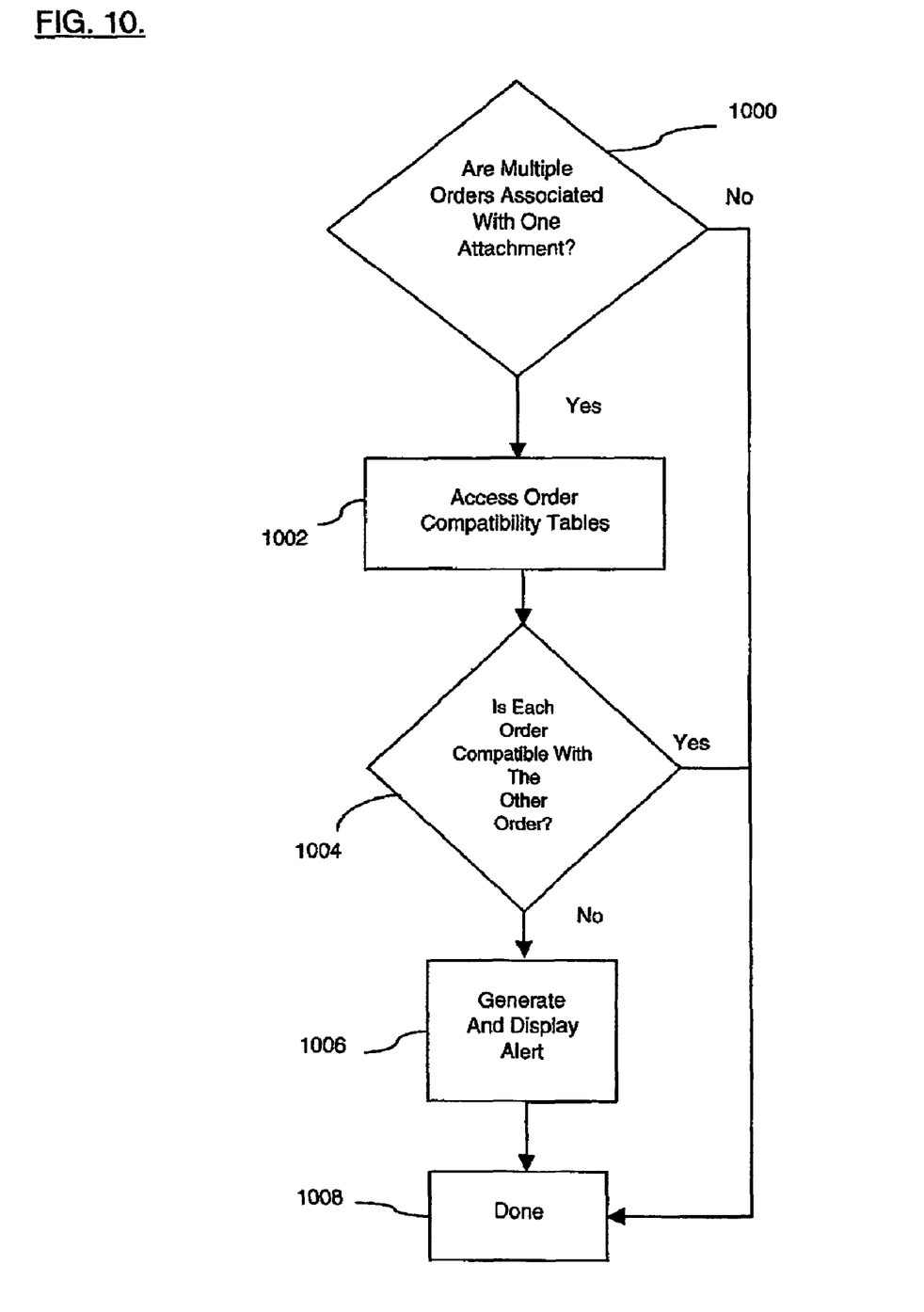
FIG. 10 is a flow diagram illustrating a preferred method for reducing the risk of adverse events attributable to the use of a common attachment for multiple orders.

As would be understood by those of skill in the art, the information received about the attachments may be stored in the database cluster of the operating environment. By associating multiple orders with one attachment in the data structure, additional safety advantages may be realized through the method of FIG. 10. First, at step 1000, the system determines if multiple orders are associated with one attachment. If so, at step 1002, the system accesses order compatibility tables. A number of medications are known to be incapable of being mixed or otherwise delivered through a common attachment. For example, an admixture of calcium and phosphate in IV fluids can lead to phosphate precipitation. Thus, medications that are unsafe to mix are compiled on a table in the database cluster of the system. Next, at step 1004, the system determines if each order associated with the attachment is compatible with each other order associated with the attachment. This step is performed by checking the associations on the order compatibility tables. If the medications (or other components) of the orders are compatible, then the system proceeds. If not, then the system generates and displays an alert to the user at step 1006. The alert is preferably a message displayed prominently on the interface of the attachment management view. Alternatively, other clinical actions may be initiated when an incompatibility is detected by the system such as sending directions to a pump to stop delivering the IV.

As known in the art, drug-drug compatibility testing is known in the art of prescription writing. Use of the system and method of the present invention extends this compatibility testing to medications that are incompatibility when administered through a common attachment. By preventing the mixture of incompatible drugs in an attachment, patient safety is improved.

Although the invention has been described with reference to the preferred embodiment illustrated in the attached drawing figures, it is noted that substitutions may be made and equivalents employed herein without departing form the scope of the invention as recited in the claims. For example, additional steps may be added and steps omitted without departing from the scope of the invention.

What the invention claimed is:

1. A method in a computer system for reducing the risk of adverse clinical events when administering multiple medications to a patient through a common attachment, comprising:
   receiving, via a hospital computing device, a selection of a designated location of a representation of at least a portion of a human body to initiate an attachment, the selection of the designated location causing a graphical indicia indicative of a location of the attachment on the patient to appear at the designated location;
   associating, via the hospital computing device, a first medication order for a first medication with the attachment using the graphical indicia;
   associating, via the hospital computing device, a second medication order for a second medication with the attachment using the graphical indicia;
   determining, via the hospital computing device, whether the first medication and the second medication are compatible with one another when the first medication and the second medication are administered through the attachment, if not, generating an alert; and
   using the hospital computing device to display the first medication order and an indication of the location of the attachment on the patient in a tabular form.

2. The method of claim 1, wherein the attachment is an intravenous (IV) line.

3. The method of claim 1, further comprising receiving order details for the first medication after the selection is received.

4. The method of claim 1, wherein the graphical indicia is an icon.

5. The method of claim 1, further comprising displaying a plurality of graphical indicia indicative of the locations of a plurality of attachments on the patient.

6. A computerized system for reducing the risk of adverse clinical events when administering multiple medications to a patient through a common attachment, comprising:
- a receiving module that receives a selection of a designated location of a representation of at least a portion of a human body to initiate an attachment, the selection of the designated location causing a graphical indicia indicative of a location of the attachment on the patient to appear at the designated location;
- a first associating module that associates a first medication order for a first medication with the attachment using the graphical indicia;
- a second associating module that associates a second medication order for a second medication with the attachment using the graphical indicia;
- a determining module that determines whether the first medication and the second medication are compatible with one another when the first medication and the second medication are administered through the attachment, if not, generating an alert; and
- a computer that displays the first medication order and an indication of the location of the attachment on the patient in a tabular form.

7. The system of claim 6, wherein the attachment is an intravenous (IV) line.

8. The system of claim 6, wherein the receiving module receives order details for the first medication after the selection is received.

9. The system of claim 6, wherein the graphical indicia is an icon.

10. The system of claim 6, further comprising:
- a displaying module for displaying a plurality of graphical indicia indicative of the locations of a plurality of attachments on the patient.

11. A computer-readable storage medium having computer executable instructions for performing a method, the method comprising:
- receiving a selection of a designated location of a representation of at least a portion of a human body to initiate an attachment, the selection of the designated location causing a graphical indicia indicative of a location of the attachment on the patient to appear at the designated location;
- associating a first medication order for a first medication with the attachment using the graphical indicia;
- associating a second medication order for a second medication with the attachment using the graphical indicia;
- determining whether the first medication and the second medication are compatible with one another when the first medication and the second medication are administered through the attachment, if not, generating an alert;
- using a computer to display the first medication order and an indication of the location of the attachment on the patient in a tabular form.

12. The method of claim 11, wherein the attachment is an intravenous (IV) line.

13. The method of claim 11, further comprising receiving order details for the first medication after the selection is received.

14. The method of claim 13, wherein the graphical indicia is an icon.

15. The method of claim 11, further comprising displaying a plurality of graphical indicia indicative of the locations of a plurality of attachments on the patient.

* * * * *